(12) United States Patent
Wilkinson et al.

(10) Patent No.: US 8,894,951 B2
(45) Date of Patent: Nov. 25, 2014

(54) SPECIMEN COLLECTION CONTAINER HAVING A TRANSITIONAL FILL-VOLUME INDICATOR INDICATING EXTRACTION METHOD

(71) Applicant: Becton, Dickinson and Company, Franklin Lakes, NJ (US)

(72) Inventors: Bradley M. Wilkinson, North Haledon, NJ (US); Craig Owen Russ, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/892,511

(22) Filed: May 13, 2013

(65) Prior Publication Data

US 2013/0252345 A1    Sep. 26, 2013

Related U.S. Application Data

(63) Continuation of application No. 13/008,479, filed on Jan. 18, 2011, now abandoned.

(60) Provisional application No. 61/296,165, filed on Jan. 19, 2010.

(51) Int. Cl.
*G01N 15/06* (2006.01)
*G01N 33/00* (2006.01)
*G01N 33/48* (2006.01)
*B01L 3/00* (2006.01)
*A61B 10/00* (2006.01)

(52) U.S. Cl.
CPC ............ *B01L 3/5082* (2013.01); *A61B 10/0096* (2013.01); *B01L 3/508* (2013.01); *A61B 2010/0093* (2013.01); *B01L 3/56* (2013.01); *B01L 2200/025* (2013.01); *B01L 2200/0605* (2013.01); *B01L 2200/14* (2013.01); *B01L 2300/0835* (2013.01); *B01L 2300/0854* (2013.01)

USPC ............ 422/554; 422/50; 422/68.1; 422/560; 422/561; 436/43; 436/63

(58) Field of Classification Search
CPC ............. B01L 9/00; B01L 3/00; G01N 21/00; A61J 1/06
USPC .......................... 422/50, 68.1, 560, 561, 554
See application file for complete search history.

(56) References Cited

U.S. PATENT DOCUMENTS 2,528,259 A   10/1950 Annunziata
3,420,107 A   1/1969 Rowett (Continued)

FOREIGN PATENT DOCUMENTS

DE   1187954 B   2/1965
EP   0224650 A2  6/1987

(Continued)

*Primary Examiner* — Brian J Sines
(74) *Attorney, Agent, or Firm* — The Webb Law Firm

(57) ABSTRACT

A specimen collection container having a transitional fill-volume indicator is disclosed. The specimen collection container includes an open top end, a closed bottom end, and a sidewall extending therebetween defining an interior. The specimen collection container includes a transitional fill-volume indicator adjacent the sidewall, such that the container defines a first volumetric interior defined by the sidewall between the closed bottom end and the transitional indicator. The specimen collection container also defines a second volumetric interior defined by the sidewall between the closed bottom end and a portion of the sidewall disposed above the transitional indicator. The first volumetric interior is adapted to allow extraction of a specimen therefrom by a first extraction process, and the second volumetric interior is adapted to allow extraction of a specimen therefrom by either the first extraction process or a second extraction process, the second extraction process being different than the first extraction process.

19 Claims, 10 Drawing Sheets

(56) References Cited

U.S. PATENT DOCUMENTS

| | | | |
|---|---|---|---|
| 4,015,352 A | 4/1977 | Prange | |
| 4,125,376 A | 11/1978 | Razulis | |
| 4,156,570 A | 5/1979 | Wardlaw | |
| 4,344,994 A | 8/1982 | Batty et al. | |
| 4,558,947 A | 12/1985 | Wardlaw | |
| 4,871,077 A | 10/1989 | Ogden et al. | |
| 4,873,193 A | 10/1989 | Jensen et al. | |
| 4,942,966 A | 7/1990 | Kemp | |
| 4,967,919 A | 11/1990 | Earhart | |
| 5,048,711 A | 9/1991 | Weiss et al. | |
| 5,061,263 A | 10/1991 | Yamazaki et al. | |
| 5,071,168 A | 12/1991 | Shamos | |
| 5,164,575 A | 11/1992 | Neeley et al. | |
| 5,178,417 A | 1/1993 | Eshoo | |
| 5,215,102 A | 6/1993 | Guirguis | |
| 5,316,952 A | 5/1994 | Brimhall | |
| 5,381,487 A | 1/1995 | Shamos | |
| 5,401,110 A | 3/1995 | Neeley | |
| 5,779,074 A | 7/1998 | Burns | |
| 5,888,184 A | 3/1999 | Wardlaw | |
| 5,889,584 A | 3/1999 | Wardlaw | |
| 6,077,235 A | 6/2000 | Serpentino et al. | |
| 6,080,366 A | 6/2000 | Kelly et al. | |
| 6,209,921 B1 | 4/2001 | Hogan et al. | |
| 6,279,759 B1 | 8/2001 | Weisbach | |
| 6,428,640 B1 | 8/2002 | Stevens et al. | |
| 6,497,325 B1 | 12/2002 | DiCesare et al. | |
| 6,551,267 B1 | 4/2003 | Cohen et al. | |
| 6,599,481 B2 | 7/2003 | Stevens et al. | |
| 6,613,410 B1 | 9/2003 | Sellars | |
| 6,651,835 B2 | 11/2003 | Iskra | |
| 6,793,075 B1 | 9/2004 | Jeter | |
| 6,910,597 B2 | 6/2005 | Iskra | |
| 7,097,057 B2 | 8/2006 | Classens | |
| 7,122,157 B2 | 10/2006 | Stevens et al. | |
| 2003/0059347 A1 | 3/2003 | Ostgaard et al. | |
| 2003/0070338 A1 | 4/2003 | Roshkoff | |
| 2003/0145945 A1 | 8/2003 | Kennedy | |
| 2004/0050846 A1 | 3/2004 | Iskra | |
| 2004/0222223 A1 | 11/2004 | Swenson | |
| 2004/0223889 A1 | 11/2004 | Reichenbach et al. | |
| 2006/0091669 A1 | 5/2006 | Wilkinson | |
| 2006/0233675 A1 | 10/2006 | Stein | |
| 2007/0134134 A1 | 6/2007 | Watts et al. | |
| 2008/0125673 A1 | 5/2008 | Carano et al. | |

FOREIGN PATENT DOCUMENTS

| | | |
|---|---|---|
| EP | 0740155 A1 | 10/1996 |
| EP | 1199104 A2 | 4/2002 |
| GB | 1425964 A | 2/1976 |
| JP | 39-013088 | 5/1939 |
| JP | 56-037058 | 8/1954 |
| JP | 63-188768 A | 8/1988 |
| JP | 09-329599 A | 12/1997 |
| JP | 2000-046825 A | 2/2000 |
| JP | 2005-172447 A | 6/2005 |
| JP | 2008-518679 A | 6/2008 |
| JP | 2009-519439 A | 5/2009 |
| JP | 2009-526231 A | 7/2009 |
| JP | 2010-502994 A | 1/2010 |
| WO | 0154816 A1 | 8/2001 |
| WO | 2004018304 A2 | 3/2004 |
| WO | 2004043601 A1 | 5/2004 |
| WO | 2005014173 A1 | 2/2005 |
| WO | 2006/050319 A2 | 5/2006 |
| WO | 2007/070740 A2 | 6/2007 |
| WO | 2008/031036 A1 | 3/2008 |

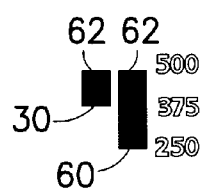 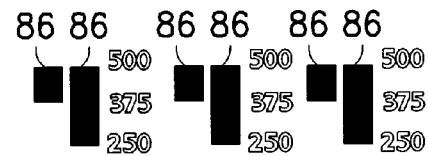
FIG.10     FIG.10A
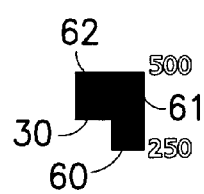 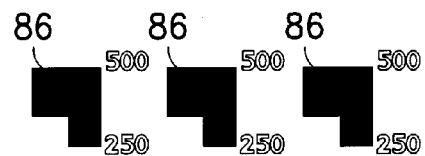
FIG.11     FIG.11A
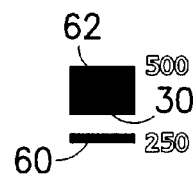 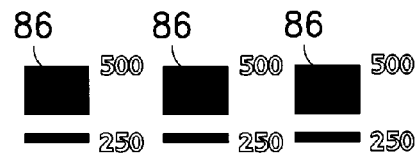
FIG.12     FIG.12A
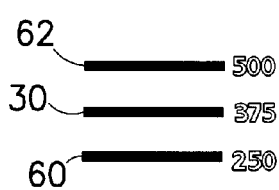 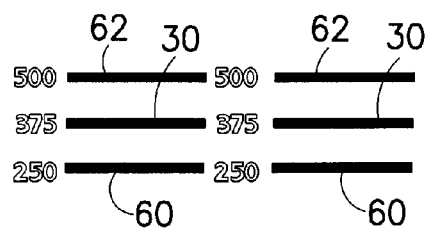
FIG.12A1     FIG.12A2

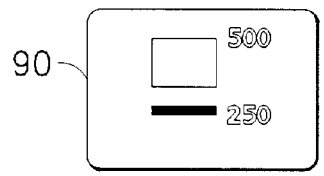 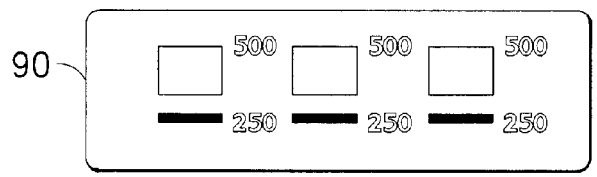
FIG.13  FIG.13A
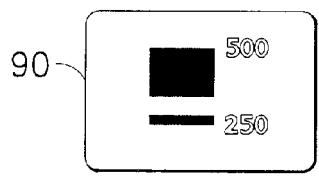 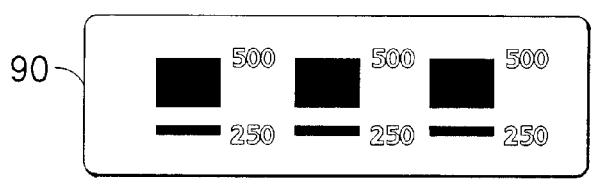
FIG.14  FIG.14A
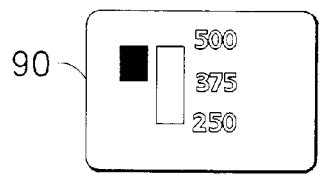 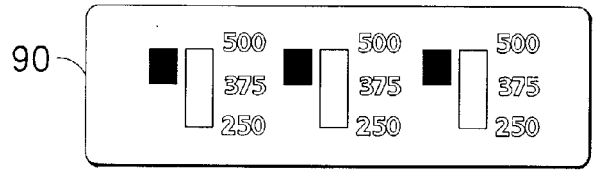
FIG.15  FIG.15A

SPECIMEN COLLECTION CONTAINER HAVING A TRANSITIONAL FILL-VOLUME INDICATOR INDICATING EXTRACTION METHOD

CROSS-REFERENCE TO RELATED APPLICATIONS

The present application is a continuation of and claims priority to U.S. application Ser. No. 13/008,479 entitled "Specimen Collection Container Having a Transitional Fill-Volume Indicator Indicating Extraction Method", filed Jan. 18, 2011, which claims priority to U.S. Provisional Application No. 61/296,165 filed Jan. 19, 2010 entitled "Specimen Collection Container Having a Transitional Fill-Volume Indicator Indicating Extraction Method", the entire disclosures of each of which are herein incorporated by reference.

BACKGROUND OF THE INVENTION

1. Field of the Invention

The present invention relates generally to specimen collection containers used to collect a fluid sample and, more particularly, to specimen collection containers having a fill-volume indicator.

2. Description of Related Art

Biological sample containers have traditionally been used for the collection of specimens, such as blood and other bodily fluids. Collected specimens are typically required for the purpose of, for example, performing diagnostic tests. In many cases, a predetermined volume of specimen is required to perform a specific test, and specimen collection containers are often utilized to facilitate collection of a precise test-specific specimen volume. In certain specimen collection containers, a pre-measured additive, such as a preservative or anticoagulant, is deposited into the container to preserve or otherwise prepare the sample. Accordingly, it is important that the amount of fluid sample collected within the container corresponds to the volume of additive within the container and/or the desired test volume.

In some cases, specimen collection containers include graduated, numerical markings on an outer surface so that a technician can visually determine the amount of volume in the container at a given time in terms of milliliters or fractions of a milliliter. In other cases, containers having simply a fill-line indicator are provided, with the fill-line indicator defining, for instance, a minimum and/or maximum amount of sample that can be placed in the container. U.S. Patent Application Publication No. 2008/0125673 provides an example of such a collection container. It is noted herein that in certain embodiments, during use of the container a medical practitioner may rely on the fill-line indicator and not on the numerical markings to determine proper fill and withdrawal of sample. Accordingly, in certain embodiments, use of the container does not require reliance on the numerical markings by a medical practitioner.

However, certain diagnostic tests require extraction of a sample from the specimen collection container manually, whereas other diagnostic tests may permit extraction of the sample from the specimen collection container for an automated process. In certain cases, both processes may be machine related, in which one process involves a user holding the sample to the probe, and the other process involves an analyzer automatically accessing the sample via a probe. In certain cases, the volume of sample required for automated extraction may be different than the volume of sample required for manual extraction. Traditional numerical indicators and min/max fill-line indicator combinations are insufficient to communicate the different fill-volumes required for manual and automatic sample extraction.

SUMMARY OF THE INVENTION

In accordance with an embodiment of the present invention, a specimen collection container includes an open top end, a closed bottom end, and a sidewall extending therebetween defining an interior. The specimen collection container also includes a transitional fill-volume indicator adjacent the sidewall. The container defines a first volumetric interior defined by the sidewall between the closed bottom end and the transitional indicator. The container also defines a second volumetric interior defined by the sidewall between the closed bottom end and a portion of the sidewall disposed above the transitional indicator. The first volumetric interior is adapted to allow extraction of a specimen therefrom by a first extraction process, and the second volumetric interior is adapted to allow extraction of a specimen therefrom by either the first extraction process or a second extraction process, with the second extraction process being different than the first extraction process.

The specimen collection container may further include an additive spray-dried to the interior, the additive provided in an appropriate amount to correspond to a volume of specimen designated by the transitional fill-volume indicator. The first extraction process may be a manual extraction process, and the second extraction process may be an automated extraction process. Optionally, the transitional fill-volume indicator may be integrally formed with the sidewall of the container. In one configuration, the transitional fill-volume indicator is at least partially raised with respect to a surface of the sidewall of the container. In another configuration, the transitional fill-volume indicator is at least partially recessed with respect to a surface of the sidewall of the container. In yet another configuration, the transitional fill-volume indicator is printed on a surface of the sidewall of the container. The transitional fill-volume indicator may be at least partially textured with respect to a surface of the sidewall of the container.

In another configuration, the transitional fill-volume indicator includes a first colored portion, and at least a portion of the sidewall of the container comprises a second colored portion, with the second colored portion being different than the first colored portion. The specimen collection container may also include a color contrast or visual effects contrast between at least a portion of the transitional fill-volume indicator and at least a portion of the sidewall of the container. The specimen collection container may also include a label including the transitional fill-volume indicator disposed at least partially on a sidewall of the container. Optionally, at least one of the label and the sidewall of the container includes first alignment symbology and the other of the label and the sidewall of the container includes second alignment symbology. The first alignment symbology and the second alignment symbology may provide corresponding alignment. The transitional fill-volume indicator may further include information identifying at least one of the first extraction process and the second extraction process. In other configurations, the specimen collection container may include a closure disposed at least partially within the open top end of the container. Optionally, the closure may include a pierceable portion capable of being pierced by a probe for automated extraction.

In accordance with another embodiment of the present invention, a specimen collection container includes an open top end, a closed bottom end, and a sidewall extending therebetween defining an interior. The specimen collection container also includes a first fill-volume indicator adjacent the sidewall corresponding to a first interior fill-volume, and a second fill-volume indicator adjacent the sidewall corresponding to a second interior fill-volume. The first interior fill-volume is less than the second interior fill-volume. The specimen collection container also includes a transitional fill-volume indicator adjacent the sidewall and positioned between the first fill-volume indicator and the second fill-volume indicator. The first fill-volume indicator, the second fill-volume indicator, and the transitional fill-volume indicator may be aligned along a longitudinal axis of the container. A sample may be extracted from within the interior of the container by a first extraction process if the volume of sample is below the transitional fill-volume indicator in a sampling orientation, and a sample may be extracted from within the interior of the container by the first extraction process or a second extraction process if the volume of sample is above the transitional fill-volume in the sampling orientation, with the second extraction process being different than the first extraction process.

The first extraction process may be a manual extraction process, and the second extraction process may be an automated extraction process. In one configuration, at least one of the first fill-volume indicator, the second fill-volume indicator, and the transitional fill-volume indicator are integrally formed with the sidewall of the container. In another configuration, at least one of the first fill-volume indicator, the second fill-volume indicator, and the transitional fill-volume indicator are at least partially raised with respect to a surface of the sidewall of the container. In yet another configuration, at least one of the first fill-volume indicator, the second fill-volume indicator, and the transitional fill-volume indicator are at least partially recessed with respect to a surface of the sidewall of the container.

Optionally, at least one of the first fill-volume indicator, the second fill-volume indicator, and the transitional fill-volume indicator are printed on a surface of the sidewall of the container. In another configuration, at least one of the first fill-volume indicator, the second fill-volume indicator, and the transitional fill-volume indicator are at least partially textured with respect to a surface of the sidewall of the container. At least one of the first fill-volume indicator, the second fill-volume indicator, and the transitional fill-volume indicator may include a color contrast or visual effects contrast with respect to at least one of a portion of the sidewall of the container and the other of the first fill-volume indicator, the second fill-volume indicator, and the transitional fill-volume indicator.

The specimen collection container may also include a label including at least one of the first fill-volume indicator, the second fill-volume indicator, and the transitional fill-volume indicator disposed at least partially on a sidewall of the container. At least one of the label and the sidewall of the container includes first alignment symbology and the other of the label and the sidewall of the container includes second alignment symbology, wherein the first alignment symbology and the second alignment symbology provide corresponding alignment. Optionally, at least one of the first fill-volume indicator, the second fill-volume indicator, and the transitional fill-volume indicator include identifying information. The identifying information may identify at least one of the first extraction process and the second extraction process. The identifying information may also identify corresponding fill-volumes.

At least one of the first fill-volume indicator, the second fill-volume indicator, and the transitional fill-volume indicator may include a line disposed substantially perpendicular to a longitudinal axis of the container. In another configuration, at least one of the first fill-volume indicator, the second fill-volume indicator, and the transitional fill-volume indicator include a window through which a specimen may be viewed. In yet another configuration, at least one of a range extending between the first fill-volume indicator and the transitional fill-volume indicator, and a range extending between the transitional fill-volume indicator and the second fill-volume indicator include an indicator region. The indicator region may include a color contrast or a visual effects contrast with at least a portion of the sidewall of the container. The indicator region may also include a window through which a specimen may be viewed. The indicator region may also include a first region corresponding to the range extending between the first fill-volume indicator and the transitional fill-volume indicator, and a second region corresponding to the range extending between the transitional fill-volume indicator and the second fill-volume indicator. Optionally, the specimen collection container may further include a closure disposed at least partially within the open top end of the container.

In accordance with yet another embodiment of the present invention, a specimen collection container includes an open top end, a closed bottom end, and a sidewall extending therebetween defining an interior. The specimen collection container also includes a minimum fill-volume indicator adjacent the sidewall, wherein the sidewall defines a minimum functional volume between the closed bottom end and the minimum fill-volume indicator. The specimen collection container also includes a maximum fill-volume indicator adjacent the sidewall, wherein the sidewall defines a maximum functional volume between the closed bottom end and the maximum fill-volume indicator. The specimen collection container further includes a transitional fill-volume indicator adjacent the sidewall and positioned between the minimum fill-volume indicator and the maximum fill-volume indicator, with the sidewall defining a first extraction volume between the minimum fill-volume indicator and the transitional fill-volume indicator. A sample may be extracted from the first extraction volume by a first extraction process. The sidewall further defines a second extraction volume between the transitional fill-volume indicator and the maximum fill-volume indicator. A sample may be extracted from the second extraction volume by either the first extraction process or a second extraction process, the second extraction process being different than the first extraction process.

The first extraction process may be a manual extraction process, and the second extraction process may be an automated extraction process.

In accordance with a further embodiment of the present invention, a method of filling a specimen collection container with a specimen includes providing a collection container having an open top end, a closed bottom end, and a sidewall extending therebetween defining an interior, with the sidewall including a transitional fill-volume indicator. The method also includes providing a volume of specimen into the interior of the container such that the volume of specimen is disposed at or below the transitional fill-volume indicator if it is desired to remove the specimen therefrom by a first extraction process. Alternatively, the method includes providing a volume of specimen into the interior of the container such that at least a portion of the volume of specimen is disposed above the transitional fill-volume indicator if it is desired to remove the specimen therefrom by a second extraction process, with the second extraction process being different than the first extraction process.

The first extraction process may be a manual extraction process, and the second extraction process may be an automated extraction process.

In accordance with yet a further embodiment of the present invention, a method of extracting a sample from a specimen collection container includes providing a collection container having an open top end, a closed bottom end, and a sidewall extending therebetween defining an interior, with the sidewall including a transitional fill-volume indicator and a specimen disposed within the interior. The method also includes extracting the specimen from the interior by a first extraction process if the specimen is disposed at or below the transitional fill-volume indicator, or extracting the specimen from the interior by a second extraction process if at least a portion of the specimen is disposed above the transitional fill-volume indicator, the second extraction process being different than the first extraction process.

The first extraction process may be a manual extraction process, and the second extraction process may be an automated extraction process.

In accordance with yet a further embodiment of the present invention, a method of producing a specimen collection container includes providing a collection container having an open top end, a closed bottom end, and a sidewall extending therebetween defining an interior. The method also includes providing a first fill-volume indicator adjacent the sidewall, and providing a second fill-volume indicator adjacent the sidewall, wherein the first fill-volume indicator and the second fill-volume indicator are positioned to share at least one common surface.

The first fill-volume indicator and the second fill-volume indicator may share at least one of a top surface and a bottom surface. The method may also include providing a transitional fill-volume indicator adjacent the sidewall, wherein the transitional fill-volume indicator is co-extensive with at least one of the first fill-volume indicator and the second fill-volume indicator. Optionally, the method may further include providing a transitional fill-volume indicator adjacent the sidewall, wherein the transitional fill-volume indicator is provided between the first fill-volume indicator and the second-fill volume indicator. The first fill-volume indicator may define a minimum functional fill-volume from the closed bottom end, and the second fill-volume indicator may define a maximum functional fill-volume from the closed bottom end.

In accordance with yet a further embodiment of the present invention, a specimen collection assembly includes a container having an open top end, a closed bottom end, and a sidewall extending therebetween defining an interior adapted to receive a sample therein. The assembly also includes a dose-specific additive disposed within the interior, and a transitional fill-volume indicator adjacent the sidewall. The container may define a first volumetric interior defined by the sidewall between the closed bottom end and the transitional fill-volume indicator, and the container may define a second volumetric interior defined by the sidewall between the closed bottom end and a portion of the sidewall disposed above the transitional indicator. The transitional fill-volume indicator may indicate the amount of sample to be introduced into the interior for a first process dependent on the dose-specific additive, and the transitional fill-volume indicator may also indicate the amount of sample to be introduced into the interior for a second process dependent on the dose-specific additive, with the first process being different from the second process.

The first process may be an extraction procedure, diagnostic, qualitative, or quantitative test procedure, and the second process may be a different extraction procedure, diagnostic, qualitative, or quantitative test procedure. Optionally, the assembly may further include a minimum fill-volume indicator adjacent the sidewall, wherein the sidewall defines a minimum functional volume between the closed bottom end and the minimum fill-volume indicator. The assembly may also include a maximum fill-volume indicator adjacent the sidewall, wherein the sidewall defines a maximum functional volume between the closed bottom end and the maximum fill-volume indicator.

BRIEF DESCRIPTION OF THE FIGURES

FIG. 10 is a schematic representation of an exemplary minimum fill-volume indicator, maximum fill-volume indicator, and transitional fill-volume indicator capable of being disposed adjacent a sidewall of a specimen collection container in accordance with an embodiment of the present invention.

FIG. 10A is a schematic representation of multiple minimum fill-volume indicators, maximum fill-volume indicators, and transitional fill-volume indicators capable of being disposed adjacent a sidewall of a specimen collection container in a wrap-around configuration in accordance with an embodiment of the present invention.

FIG. 11 is a schematic representation of an exemplary minimum fill-volume indicator, maximum fill-volume indicator, and transitional fill-volume indicator capable of being disposed adjacent a sidewall of a specimen collection container in accordance with an embodiment of the present invention.

FIG. 11A is a schematic representation of multiple minimum fill-volume indicators, maximum fill-volume indicators, and transitional fill-volume indicators capable of being disposed adjacent a sidewall of a specimen collection container in a wrap-around configuration in accordance with an embodiment of the present invention.

FIG. 12 is a schematic representation of an exemplary minimum fill-volume indicator, maximum fill-volume indicator, and transitional fill-volume indicator capable of being disposed adjacent a sidewall of a specimen collection container in accordance with an embodiment of the present invention.

FIG. 12A is a schematic representation of multiple minimum fill-volume indicators, maximum fill-volume indicators, and transitional fill-volume indicators capable of being disposed adjacent a sidewall of a specimen collection container in a wrap-around configuration in accordance with an embodiment of the present invention.

FIG. 12A1 is a schematic representation of an exemplary minimum fill-volume indicator, maximum fill-volume indicator, and transitional fill-volume indicator capable of being disposed adjacent a sidewall of a specimen collection container in accordance with an embodiment of the present invention.

FIG. 12A2 is a schematic representation of multiple minimum fill-volume indicators, maximum fill-volume indicators, and transitional fill-volume indicators capable of being disposed adjacent a sidewall of a specimen collection container in a wrap-around configuration in accordance with an embodiment of the present invention.

FIG. 13 is a schematic representation of a label having a minimum fill-volume indicator, a maximum fill-volume indicator, and a transitional fill-volume indicator capable of being disposed adjacent a sidewall of a collection container in accordance with an embodiment of the present invention.

FIG. 13A is a schematic representation of a label having multiple minimum fill-volume indicators, maximum fill-volume indicators, and transitional fill-volume indicators in accordance with an embodiment of the present invention.

FIG. 14 is a schematic representation of a label having a minimum fill-volume indicator, a maximum fill-volume indicator, and a transitional fill-volume indicator capable of being disposed adjacent a sidewall of a collection container in accordance with an embodiment of the present invention.

FIG. 14A is a schematic representation of a label having multiple minimum fill-volume indicators, maximum fill-volume indicators, and transitional fill-volume indicators in accordance with an embodiment of the present invention.

FIG. 15 is a schematic representation of a label having a minimum fill-volume indicator, a maximum fill-volume indicator, and a transitional fill-volume indicator capable of being disposed adjacent a sidewall of a collection container in accordance with an embodiment of the present invention.

FIG. 15A is a schematic representation of a label having multiple minimum fill-volume indicators, maximum fill-volume indicators, and transitional fill-volume indicators in accordance with an embodiment of the present invention.

DETAILED DESCRIPTION OF THE PREFERRED EMBODIMENTS

For purposes of the description hereinafter, spatial orientation terms, if used, shall relate to the referenced embodiment, device, component, or feature as it is oriented in the accompanying drawing figures or otherwise described in the following detailed description. However, it is to be understood that the embodiments, devices, components, or features described herein may assume many alternative variations. It is also to be understood that the specific embodiments, devices, components, and features illustrated in the accompanying drawing figures and described herein are simply exemplary and should not be considered as limiting.

The present invention relates to specimen collection containers used in collecting a fluid sample, such as blood or other biological fluid samples. The specimen collection containers of the present invention include a transitional fill-volume indicator for visually conveying to a medical practitioner responsible for drawing the sample the appropriate amount of sample that should be collected given the future intended processing method and/or future intended extraction method for removing the sample from the specimen collection container. The transitional fill-volume indicator also indicates to the technician charged with performing diagnostic testing of the sample which extraction method may be used to withdraw the sample from the specimen collection container based on the amount of sample present in the specimen collection container. The specimen collection containers of the present invention are particularly useful where the amount of sample in the specimen collection container dictates how the sample is subsequently analyzed, such as whether the sample is withdrawn from the specimen collection container by a manual or an automatic extraction process. Some diagnostic equipment may also be capable of processing a fluid sample in either an "automatic" or "manual" sampling mode, with the particular mode being at least partially dependent on the volume of sample in the container.

Figure 1:
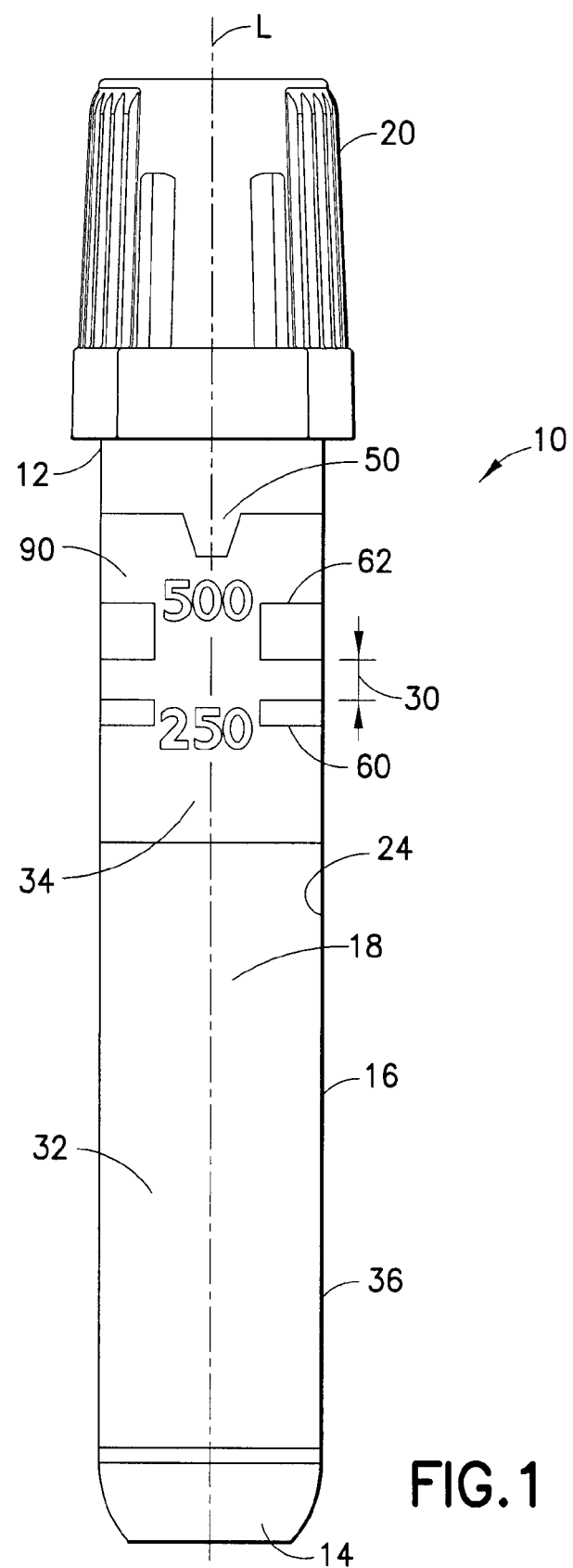
FIG. 1 is a perspective view of specimen collection container having a closure and a transitional fill-volume indicator adjacent a sidewall of the specimen collection container in accordance with an embodiment of the present invention.
Figure 2:
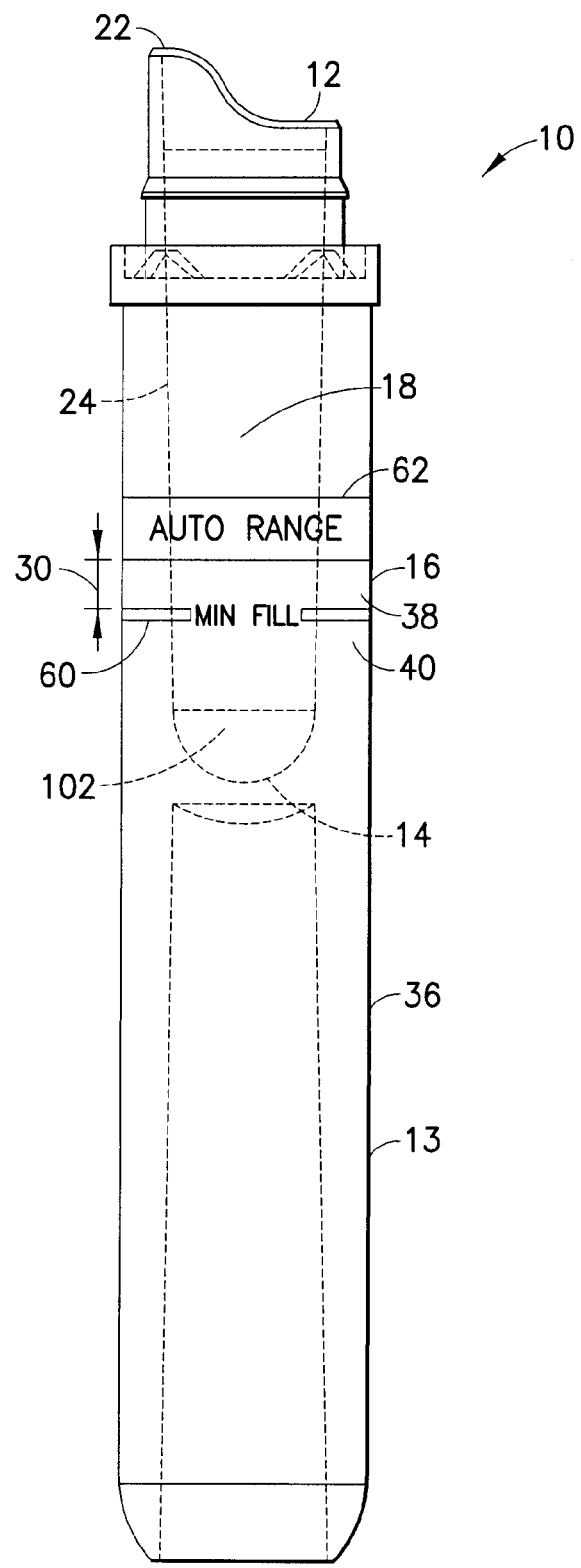
FIG. 2 is a front view of a specimen collection container having an alternative transitional fill-volume indicator in accordance with an embodiment of the present invention.
Figure 3:
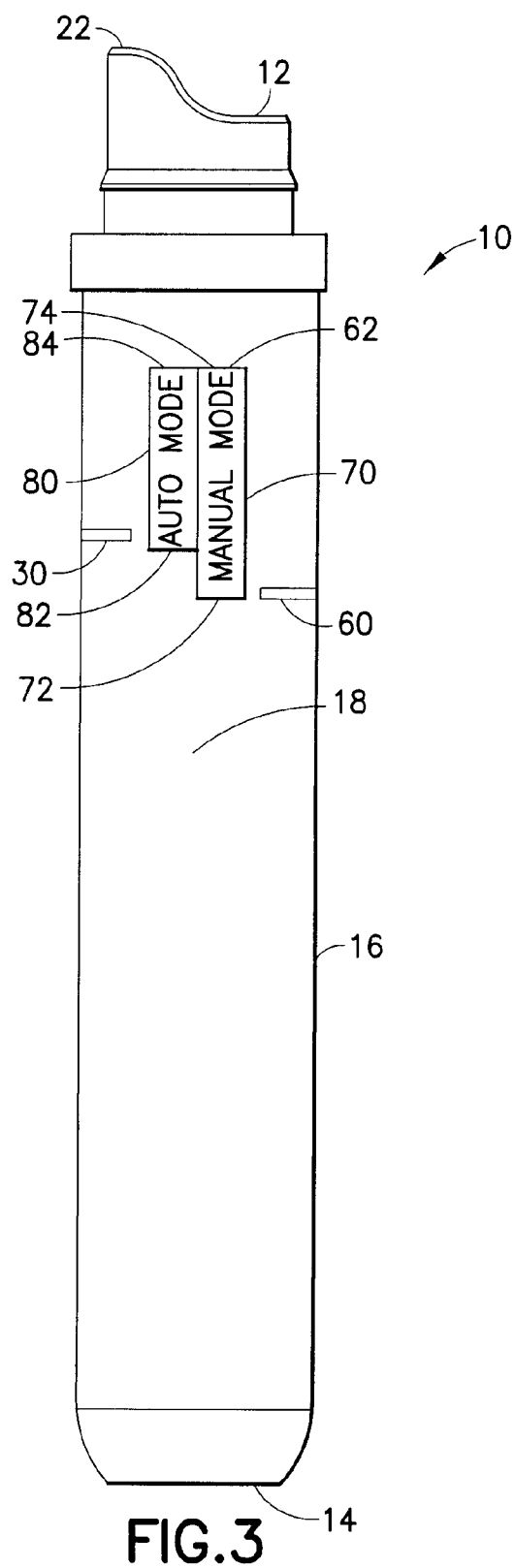
FIG. 3 is a front view of a specimen collection container having an alternative transitional fill-volume indicator in accordance with an embodiment of the present invention.

With reference to FIGS. 1-3, a specimen collection container 10 for collecting a fluid sample, such as a blood sample, is generally shown. Specimen collection container 10 includes an open top end 12, a closed bottom end 14, and a sidewall 16 extending therebetween, defining an interior 18. In certain embodiments, the open top end 12 may be covered by a closure 20, such as a removable cap. In other embodiments, the closure 20 may include a pierceable septum which may be pierced by a standard needle cannula to introduce a sample into the interior and/or pierced by a needle cannula or probe to withdraw a sample from the interior. The pierceable septum may be a re-sealable septum permitting piercing by a needle cannula to introduce a specimen into the interior and subsequent re-sealing of the septum. The pierceable septum may optionally be re-pierced by another needle cannula or probe to withdraw the sample from the interior. The pierceable septum or pierceable portion of the closure 20 may be capable of being pierced by a probe for automated extraction. The specimen collection container 10 may be any suitable container adapted to receive a fluid sample therein, such as a blood collection tube.

In one embodiment, the specimen collection container 10 is a small volume blood collection container having an interior fill-volume of from about 500 µl to about 1.5 ml. In another embodiment, the specimen collection container 10 may have a larger interior fill-volume, such as from about 8 ml to about 10 ml. As shown in FIGS. 2-3, the specimen collection container 10 may also include a curved receiving portion 22, defining a generally scooped portion, which may facilitate collection of a specimen into the container interior 18. If the desired specimen to be collected is blood from a patient's capillary or venous blood from a fragile vein patient, then the closure 20 of the specimen collection container 10 may be removed and the curved receiving portion 22 may be positioned adjacent the blood collection site to facilitate introduction of blood into the interior 18 of the specimen collection container 10. Referring specifically to FIG. 2, in certain embodiments, the specimen collection container 10 may have an interior fill-volume which corresponds to a small-volume collection container (such as from about 500 μl, to about 1.5 ml) but may have the external dimensions of a large-volume collection container (such as having a length of about 10 cm and a diameter of about 16 mm) in order to accommodate standard diagnostics processing equipment. In this configuration, the specimen collection container 10 may include a false bottom 13 which may extend longitudinally beyond the interior 18 of the specimen collection container 10.

The specimen collection container 10 may be made of any suitable liquid and/or gas impermeable material, such as glass and/or polymeric compositions. In addition, an interior surface 24 of the sidewall 16 may be coated with a barrier coating having liquid and/or gas retention properties. In one embodiment, the barrier coating may provide improved oxygen and water retention properties, and may be applied via spray coating or brushing. In another configuration, the sidewall 16 may include a "double-wall" construction in which a second sidewall circumferentially surrounds a first sidewall in order to provide an air barrier therebetween to improve the barrier properties of the specimen collection container 10.

In yet another embodiment, the interior 18 of the specimen collection container 10 can be provided with an additive for imparting desired properties to the sample collected therein. For example, one or more additives such as reagents, preservatives, anticoagulants, coagulants, clot activators, and/or other known additives may be provided within the interior 18 of the specimen collection container 10 to provide for a desired effect on the sample. Desirably, such additives are provided in dry form such as a powder or pellet. The additive may be spray-dried to the interior of the collection container 10. In one embodiment, the additive may be provided in an appropriate amount to correspond to a volume of specimen designated by a transitional fill-volume indicator 30.

Referring again to FIGS. 1-3, the specimen collection container 10 may include a transitional fill-volume indicator 30 adjacent the sidewall 16. When the specimen collection container 10 is positioned in a sampling orientation, such as substantially upright along the longitudinal axis L, and a sample is disposed within the interior 18, the transitional fill-volume indicator 30 indicates whether there is sufficient sample volume within the specimen collection container 10 to be extracted by a first extraction process, or whether there is sufficient sample volume within the specimen collection container 10 to be extracted by a second extraction process. For example, if the volume of sample disposed within the interior 18 is disposed entirely below the transitional fill-volume indicator 30, then the sample must be extracted from the specimen collection container 10 by the first extraction process. If the volume of sample disposed within the interior 18 is disposed at least partially at or above the transitional fill-volume indicator 30, then the sample may be extracted from the specimen collection container 10 by either the first extraction process or a second extraction process, in which the second extraction process is different than the first extraction process. In certain configurations, if the sample volume is disposed entirely below the transitional fill-volume indicator 30, then the sample must be extracted from the specimen collection container 10 by a manual extraction process, such as by manual pipetting or other extraction procedures. If the sample volume is disposed at least partially above the transitional fill-volume indicator 30, then the sample may be extracted by either a manual extraction process or by an automated procedure in which a diagnostics machine is programmed to perform the extraction process.

As shown in FIG. 1, the specimen collection container 10 may define a first volumetric interior 32 defined by the interior surface 24 of the sidewall 16 between the closed bottom end 14 and the transitional fill-volume indicator 30. The specimen collection container 10 may also define a second volumetric interior 34 defined by the interior surface 24 of the sidewall 16 between the closed bottom end 14 and a portion of the sidewall 16 disposed above the transitional fill-volume indicator 30. In this configuration, the first volumetric interior is less than the second volumetric interior. The first volumetric interior may permit a volume of specimen to be withdrawn therefrom by the first extraction process, such as manual withdrawal, whereas the second volumetric interior may permit a volume of specimen to be withdrawn therefrom by either the first extraction process, such as manual withdrawal, or by the second extraction process, such as automatic withdrawal. In this capacity, the transitional fill-volume indicator 30 may correspond to the minimum sample volume required for extraction by an automatic process.

In one embodiment, the transitional fill-volume indicator 30 may be integrally formed with the sidewall 16 of the specimen collection container 10. The transitional fill-volume indicator 30 may include a band circumferentially disposed about the longitudinal axis L of the specimen collection container 10. The transitional fill-volume indicator 30 may be substantially continuous or may include segmented regions. Optionally, the transitional fill-volume indicator 30 may be at least partially raised with respect to a portion of an outer surface 36 of the sidewall 16, such that a medical practitioner may appreciate a tactile distinction between the transitional fill-volume indicator 30 and the sidewall 16 of the specimen collection container 10. Alternatively, the transitional fill-volume indicator 30 may be at least partially recessed with respect to a portion of the outer surface 36 of the sidewall 16, such that a medical practitioner may appreciate a tactile distinction between the transitional fill-volume indicator 30 and the sidewall 16 of the specimen collection container 10. The height of such a raised portion or depth of such a recessed portion may be any desired amount, so long as the dimensions provide a unique identifier to the human eye and/or machine processing which differentiates the raised or recessed portion from the sidewall 16 of the container 10.

In other configurations, the transitional fill-volume indicator 30 may be printed or otherwise deposited on a surface of the sidewall 16 of the specimen collection container 10. The transitional fill-volume indicator 30 may also be at least partially textured with respect to a surface of the sidewall 16 of the specimen collection container 10, such that the transitional fill-volume indicator 30 may include a roughened surface and the remaining sidewall 16 may include a substantially smooth surface. The transitional fill-volume indicator 30 may also include a first colored portion 38 and at least a portion of the sidewall 16 of the specimen collection container 10 includes a second colored portion 40, with the second colored portion 40 being different than the first colored portion 38. For example, the transitional fill-volume indicator 30 may be a colored band circumferentially extending about the sidewall 16. The sidewall 16 may be a clear or other colored appearance or portion adjacent the transitional fill-volume indicator 30. In another embodiment, the specimen collection container 10 may include a color contrast or visual effects contrast between at least a portion of the transitional fill-volume indicator 30 and at least a portion of the sidewall 16 of the specimen collection container 10. Examples of color contrasts may include contrasting color portions or variations in hue and/or intensity of the same color. Examples of visual effects contrasts may include the presence of a color modifier, such as pearlesence, sheen, metallicizers, and the like. In a further embodiment, the transitional fill-volume indicator 30 can be formed by spraying, stenciling, or otherwise applying the appropriate markings directly to a surface of the sidewall 16 of the specimen collection container 10, such as the outer surface 36 of the sidewall 16. The transitional fill-volume indicator 30 can also be formed by roughening or otherwise modifying a portion of the sidewall 16 of the specimen collection container 10 to impart a distinct visual appearance and/or texture as compared with an adjacent portion of the sidewall 16. For example, the transitional fill-volume indicator 30 may be formed by electrical discharge machining, etching, or other similar process to impart a textured appearance.

Figure 4:
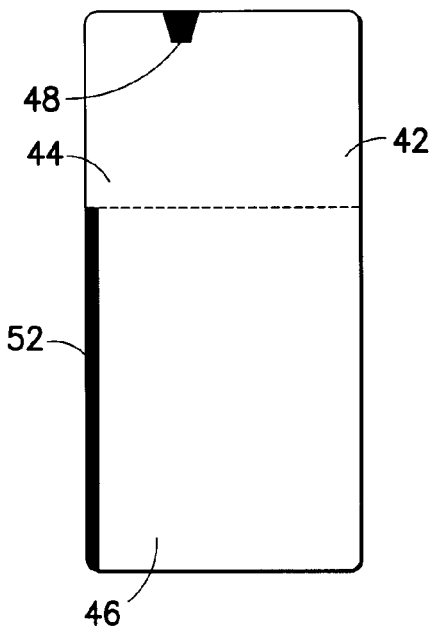
FIG. 4 is a front view of a label having alignment features for aligning with a specimen collection container in accordance with an embodiment of the present invention.
Figure 4A:
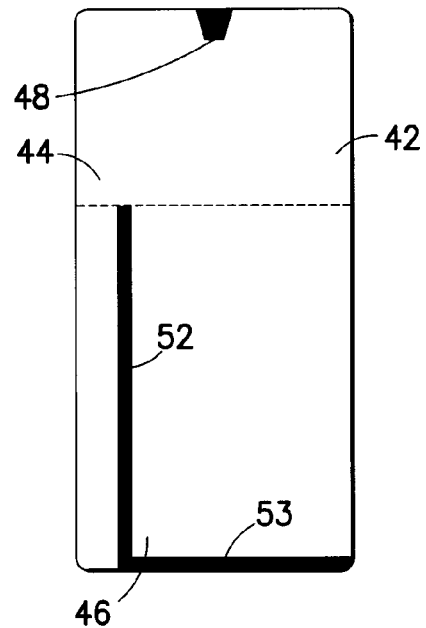
FIG. 4A is a front view of a label having alignment features for aligning with a specimen collection container in accordance with an embodiment of the present invention.
Figure 5:
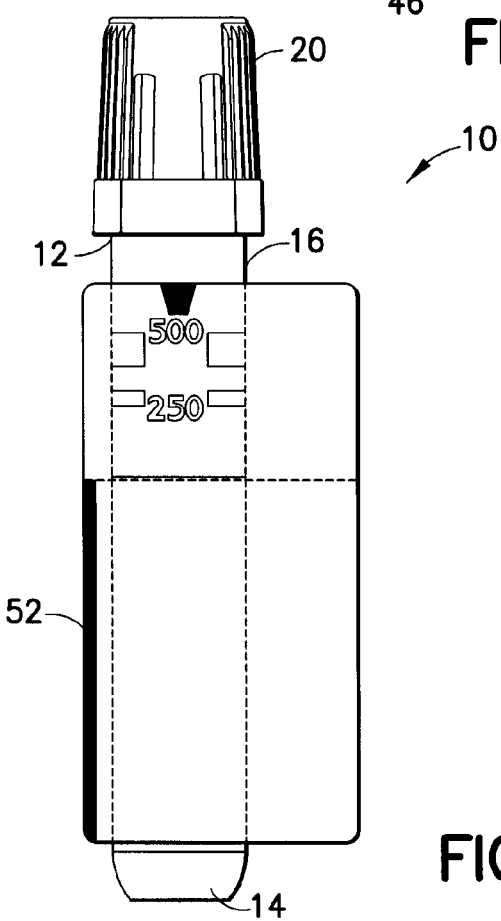
FIG. 5 is a front view of the label of FIG. 4 partially applied to the specimen collection container of FIG. 1.

As shown in FIGS. 4-5, the specimen collection container 10 may include a label 42 having identifying information thereon pertaining to patient information, testing information, and/or sampling dates. The label 42 may include a clear portion 44 and a writeable/printable portion 46 including the identifying information. The label 42 may include a first alignment symbology 48 for alignment with a portion of the specimen collection container 10 to ensure proper orientation of the label 42 with respect to the specimen collection container 10. Referring to FIG. 1, the specimen collection container 10 may also include a second alignment symbology 50, wherein alignment of the first alignment symbology 48 and the second alignment symbology 50 ensures proper alignment of the label 42 with respect to the specimen collection container 10. In one configuration, the first alignment symbology 48 may include a shaped or colored portion, and the second alignment symbology 50 may include a corresponding receiving portion adapted to receive the first alignment symbology 48 within the confines of the second alignment symbology 50. In another configuration, the first alignment symbology 48 may be provided to overlap with second alignment symbology 50 within the boundaries or perimeter of the second alignment symbology 50, as shown in FIG. 5. As shown in FIG. 4, the label 42 may include a second alignment feature 52, such as an alignment bar disposed substantially longitudinally along a portion of the label 42 to indicate proper alignment of the label 42 with respect to the specimen collection container 10. As shown in FIG. 4A, the label 42 may include a second alignment feature 52 positioned at a location that is inset from an edge of the label. Referring again to FIG. 4A, the label 42 may also include a third alignment feature 53, such as an alignment bar disposed substantially horizontally along a portion of the label 42. The second alignment feature 52 and the third alignment feature 53 may be provided to contact each other, or may be provided as discrete features. In one embodiment, the second alignment feature 52 and the third alignment feature may have a substantially identical coloration. In another embodiment, the second alignment feature 52 and the third alignment feature 53 may indicate proper alignment of the label 42 with respect to a specimen collection container, as shown in FIG. 1.

Referring again to FIGS. 1-3, the specimen collection container 10 may also include a first fill-volume indicator 60 adjacent the sidewall 16 which may correspond to a minimum fill volume. The first fill-volume indicator 60 provides an indication as to the minimum amount of a fluid sample that should be introduced into the interior 18 of the specimen collection container 10 when the specimen collection container 10 is positioned in the sampling orientation. In this manner, the first fill-volume indicator 60 provides a visual confirmation as to whether the desired minimum amount of a fluid sample has been added to the specimen collection container 10.

The specimen collection container 10 may also include a second fill-volume indicator 62 adjacent the sidewall 16 which may correspond to a maximum fill volume. The second fill-volume indicator 62 provides an indication as to the maximum amount of a fluid sample that should be introduced into the interior 18 of the specimen collection container 10 when the specimen collection container 10 is positioned in the sampling orientation. In this manner, the second fill-volume indicator 62 provides a visual confirmation as to whether the desired maximum amount of a fluid sample has been added to the specimen collection container 10.

The specimen collection container 10 may include a first fill-volume indicator 60, a second fill-volume indicator 62, and a transitional fill-volume indicator 30. In one embodiment the first fill-volume indicator 60, the second fill-volume indicator 62, and the transitional fill-volume indicator 30 are each aligned circumferentially about the longitudinal axis of the specimen collection container 10. The transitional fill-volume indicator 30 may be disposed between the first fill-volume indicator 60 and the second fill-volume indicator 62.

When the specimen collection container 10 is in the sampling orientation, the transitional fill-volume indicator 30 provides visual confirmation as to whether the amount of fluid sample that is contained within the specimen collection container 10 is sufficient to be extracted by manual or automatic extraction processes. For example, in certain situations, if the amount of sample in the container is less than the volume level defined by the transitional fill-volume indicator 30 but greater than the volume level defined by the first fill-volume indicator 60, then the sample in the container cannot be extracted by automatic extraction processes but may be extracted my manual means. If the amount of sample in the container is equal to or greater than the volume level defined by the transitional fill-volume indicator 30 and less than the volume level defined by the second fill-volume indicator 62, then the sample in the container can be extracted by either automatic extraction processes or by manual extraction means. Accordingly, a specimen collection container 10 having a transitional fill-volume indicator 30, as shown in FIGS. 1-3, greatly reduces the guesswork involved in determining whether a fluid sample contained within a container is sufficient to process that sample using a specific extraction process.

With continued reference to FIGS. 1-3, in some non-limiting embodiments, the specimen collection container 10 may include one or more, such as two, fill-volume ranges. Each of the fill-volume ranges independently defines a continuous scope or range of volume amounts, and is bounded at one end by a lower limit and bounded at the other end by an upper limit. Each of the fill-volume ranges can be associated with a respective extraction methodology such that the volumes within a particular fill-volume range reflect the acceptable sample volumes corresponding to a particular extraction process.

For instance, as shown in FIG. 3, the specimen collection container 10 may include a first fill-volume indicator range 70, bounded by a lower limit 72 and an upper limit 74, and the first fill-volume range 70 may define the appropriate sample fill volume for extraction by manual processes. Thus, if the volume of sample in the specimen collection container 10 falls within the first fill-volume indicator range 70, it would be understood that the sample could be extracted by the first extraction process, such as manual extraction. The specimen collection container 10 may further include a second fill-volume indicator range 80, also bounded by a lower limit 82, which coincides with the transitional fill-volume indicator 30, and an upper limit 84. The second fill-volume range 80 may define the appropriate sample fill volume for extraction by automatic (or manual) extraction processes. Thus, if the volume of sample in the specimen collection container 10 falls within the second fill-volume indicator range 80, it would be understood that the sample could be extracted by the first extraction process, such as manual extraction, or the second extraction process, such as automatic extraction. While the first fill-volume indicator range 70 and the second fill-volume indicator range 80 do not entirely overlap, there can be some overlap between them.

In certain configurations, the specimen collection container 10 may include a dose-specific additive 102, as shown in FIG. 2, disposed within the interior of the container 10. A dose-specific additive 102 may be any additive as described herein which is measured for interaction or activation with a specific quantity of sample, such as blood. In this configuration, the transitional fill-volume indicator 30 defines a first volumetric interior 32 by the sidewall between the closed bottom end 14 and the transitional fill-volume indicator 30. The transitional fill-volume indicator 30 also defines a second volumetric interior 34 by the sidewall between the closed bottom end 14 and a portion of the sidewall disposed above the transitional indicator 30. The transitional fill-volume indicator 30 indicates the amount of sample to be introduced into the interior for a first process dependent on the dose-specific additive, and the transitional fill-volume indicator 30 indicates the amount of sample to be introduced into the interior for a second process dependent on the dose-specific additive, with the first process being different from the second process. The first process may be, for example, an extraction procedure, diagnostic, qualitative, or quantitative test procedure, and the second process may be a different extraction procedure, diagnostic, qualitative, or quantitative test procedure.

In accordance with one embodiment of the present invention, at least one of the first fill-volume indicator 60, the second fill-volume indicator 62, and the transitional fill-volume indicator 30 are integrally formed with the sidewall 16 of the specimen collection container 10. Optionally, at least one of the first fill-volume indicator 60, the second fill-volume indicator 62, and the transitional fill-volume indicator 30 are at least partially raised with respect to an outer surface 36 of the sidewall 16 of the specimen collection container 10. Alternatively, at least one of the first fill-volume indicator 60, the second fill-volume indicator 62, and the transitional fill-volume indicator 30 are at least partially recessed with respect to an outer surface 36 of the sidewall 16 of the container 10.

In a further configuration, at least one of the first fill-volume indicator 60, the second fill-volume indicator 62, and the transitional fill-volume indicator 30 are printed or otherwise applied to a surface of the sidewall 16 of the container 10. Optionally, at least one of the first fill-volume indicator 60, the second fill-volume indicator 62, and the transitional fill-volume indicator 30 are at least partially textured with respect to a portion of a surface of the sidewall 16 of the specimen collection container 10. Further, at least one of the first fill-volume indicator 60, the second fill-volume indicator 62, and the transitional fill-volume indicator 30 may include a color contrast or visual effects contrast, as discussed above, with respect to at least a portion of the sidewall 16 of the specimen collection container 10, the other of the first fill-volume indicator 60, the second fill-volume indicator 62, and the transitional fill-volume indicator 30.

Figure 6:
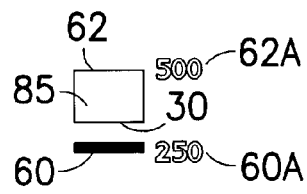
FIG. 6 is a schematic representation of an exemplary minimum fill-volume indicator, maximum fill-volume indicator, and transitional fill-volume indicator capable of being disposed adjacent a sidewall of a specimen collection container in accordance with an embodiment of the present invention.
Figure 6A:
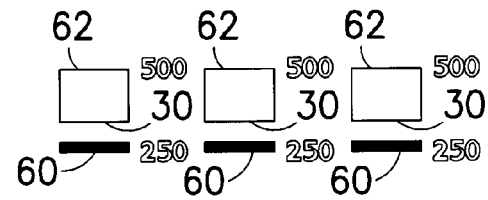
FIG. 6A is a schematic representation of multiple minimum fill-volume indicators, maximum fill-volume indicators, and transitional fill-volume indicators capable of being disposed adjacent a sidewall of a specimen collection container in a wrap-around configuration in accordance with an embodiment of the present invention.

As shown in FIGS. 6-12A2, the first fill-volume indicator 60, the second fill-volume indicator 62, and the transitional fill-volume indicator 30 may take the form of many different configurations. As shown in FIG. 6, the first fill-volume indicator 60 may take the form of a line disposed substantially perpendicular, such as substantially horizontal, with respect to the longitudinal axis L of the container, as shown in FIG. 1, and may optionally include identifying information 60A associated therewith. In one embodiment, the identifying information 60A may identify the corresponding fill volume, such as a minimum fill volume of 250 µl. Referring again to FIG. 6, the second fill-volume indicator 62 may take the form of an upper surface of a viewing window 85 formed with the transitional fill-volume indicator 30 evidencing the volume of sample required for automatic extraction of the sample from the specimen collection container 10. Optionally, the second fill-volume indicator 62 may include identifying information 62A, such as a maximum fill volume of 500 µl. As shown in FIG. 6A, the first fill-volume indicator 60, the second fill-volume indicator 62, and the transitional fill-volume indicator 30 may be repeated, such that when viewed on a specimen collection container, each of the indicators are viewable about the circumference of the sidewall.

Figure 7:
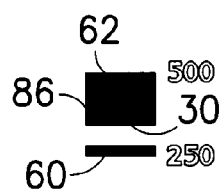
FIG. 7 is a schematic representation of an exemplary minimum fill-volume indicator, maximum fill-volume indicator, and transitional fill-volume indicator capable of being disposed adjacent a sidewall of a specimen collection container in accordance with an embodiment of the present invention.
Figure 7A:
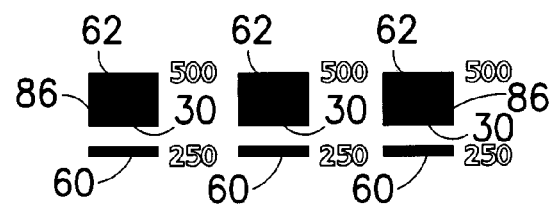
FIG. 7A is a schematic representation of multiple minimum fill-volume indicators, maximum fill-volume indicators, and transitional fill-volume indicators capable of being disposed adjacent a sidewall of a specimen collection container in a wrap-around configuration in accordance with an embodiment of the present invention.
Figure 8:
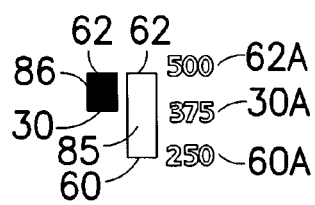
FIG. 8 is a schematic representation of an exemplary minimum fill-volume indicator, maximum fill-volume indicator, and transitional fill-volume indicator capable of being disposed adjacent a sidewall of a specimen collection container in accordance with an embodiment of the present invention.
Figure 8A:
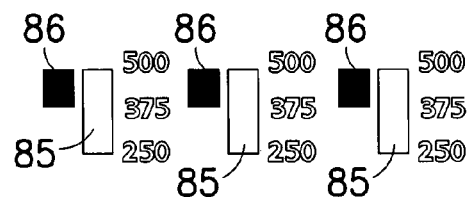
FIG. 8A is a schematic representation of multiple minimum fill-volume indicators, maximum fill-volume indicators, and transitional fill-volume indicators capable of being disposed adjacent a sidewall of a specimen collection container in a wrap-around configuration in accordance with an embodiment of the present invention.

In another configuration, as shown in FIGS. 7 and 7A, the second fill-volume indicator 62 may take the form of an upper surface of an opaque indicator region 86 formed with the transitional fill-volume indicator 30 evidencing the volume of sample required for automatic extraction of the sample from the specimen collection container 10. Optionally, the indicator region 86 may include a color contrast or visual effects contrast, as discussed herein. As shown in FIGS. 8 and 8A, the first fill-volume indicator 60 may form the bottom surface of a viewing window 85 formed with the second fill-volume indicator 62 as the top surface, which corresponds to the range of sample which may be withdrawn by a first extraction process, such as a manual extraction process. The transitional fill-volume indicator 30 may form the bottom surface of an opaque indicator region 86 formed with the second fill-volume indicator 62 as the top surface, which corresponds to the range of sample which may be withdrawn by a second extraction process, such as an automatic extraction process, or a first extraction process, such as a manual extraction process. It is noted herein, that the transitional fill-volume indicator 30 may have identifying information associated therewith, such as a transitional fill volume of 375 µl corresponding to the transitional volume needed for automatic extraction processes.

Figure 9:
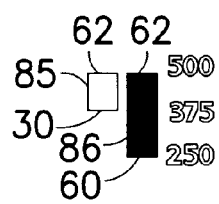
FIG. 9 is a schematic representation of an exemplary minimum fill-volume indicator, maximum fill-volume indicator, and transitional fill-volume indicator capable of being disposed adjacent a sidewall of a specimen collection container in accordance with an embodiment of the present invention.
Figure 9A:
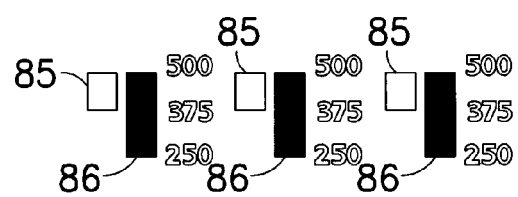
FIG. 9A is a schematic representation of multiple minimum fill-volume indicators, maximum fill-volume indicators, and transitional fill-volume indicators capable of being disposed adjacent a sidewall of a specimen collection container in a wrap-around configuration in accordance with an embodiment of the present invention.

FIGS. 9 and 9A show a similar embodiment, with the viewing window 85 formed by the transitional fill-volume indicator 30 and the second fill-volume indicator 62, and the opaque indicator region 86 formed by the first fill-volume indicator 60 and the second fill-volume indicator 62. As shown in FIGS. 10-12A, various configurations including an opaque indicator region(s) 86 may be shown to indicate the manual extraction process and the automatic extraction process defined by the first fill-volume indicator 60, the second fill-volume indicator 62, and the transitional fill-volume indicator 30. As shown in FIG. 11, in certain configurations, the profiles of the first fill-volume indicator 60 and the second fill-volume indicator 62 share at least one common surface 61. In this configuration, the transitional fill-volume indicator 30 may be co-extensive with at least a portion of the first fill-volume indicator 60 and/or the second fill-volume indicator 62.

As shown in FIG. 12A1, the first fill-volume indicator 60 may take the form of a line disposed substantially perpendicular, such as substantially horizontal, with respect to the longitudinal axis L of the container, as shown in FIG. 1, and may optionally include identifying information associated therewith, as described herein. The second fill-volume indicator 62 may also take the form of a line disposed substantially perpendicular to the first fill-volume indicator 60 and may be positioned above the first fill-volume indicator 60 with respect to the longitudinal axis L of the container, also shown in FIG. 1. Optionally, the second fill-volume indicator 62 may include identifying information, as also described herein. The transitional fill-volume indicator 30 may also take the form of a line disposed substantially perpendicular to the first fill-volume indicator and may be disposed between the first fill-volume indicator 60 and the second fill-volume indicator 62. As shown in FIG. 12A2, the first fill-volume indicator 60, the second fill-volume indicator 62, and the transitional fill-volume indicator 30 may be repeated, such that when viewed on a specimen collection container, each of the indicators are viewable about the circumference of the sidewall.

Figure 12B:
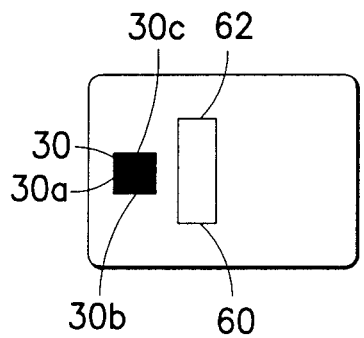
FIG. 12B is a schematic representation of an exemplary minimum fill-volume indicator, maximum fill-volume indicator, and transitional fill-volume indicator capable of being disposed adjacent a sidewall of a specimen collection container in accordance with an embodiment of the present invention.
Figure 12C:
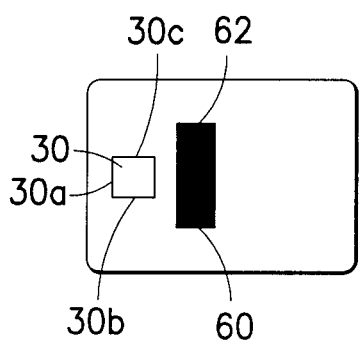
FIG. 12C is a schematic representation of an exemplary minimum fill-volume indicator, maximum fill-volume indicator, and transitional fill-volume indicator capable of being disposed adjacent a sidewall of a specimen collection container in accordance with an embodiment of the present invention.
Figure 12D:
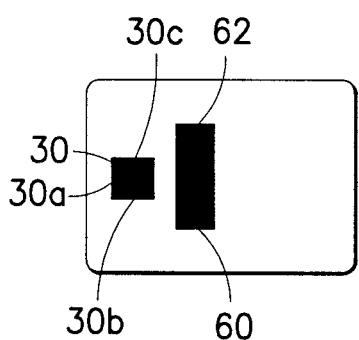
FIG. 12D is a schematic representation of an exemplary minimum fill-volume indicator, maximum fill-volume indicator, and transitional fill-volume indicator capable of being disposed adjacent a sidewall of a specimen collection container in accordance with an embodiment of the present invention.
Figure 16:
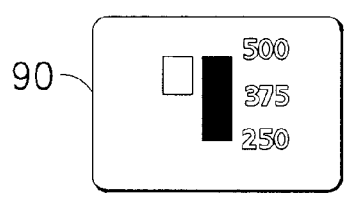
FIG. 16 is a schematic representation of a label having a minimum fill-volume indicator, a maximum fill-volume indicator, and a transitional fill-volume indicator capable of being disposed adjacent a sidewall of a collection container in accordance with an embodiment of the present invention.
Figure 16A:
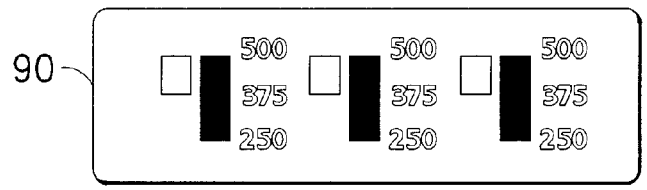
FIG. 16A is a schematic representation of a label having multiple minimum fill-volume indicators, maximum fill-volume indicators, and transitional fill-volume indicators in accordance with an embodiment of the present invention.
Figure 17:
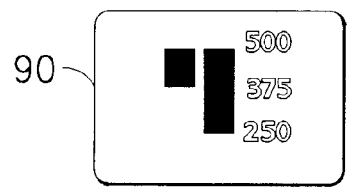
FIG. 17 is a schematic representation of a label having a minimum fill-volume indicator, a maximum fill-volume indicator, and a transitional fill-volume indicator capable of being disposed adjacent a sidewall of a collection container in accordance with an embodiment of the present invention.
Figure 17A:
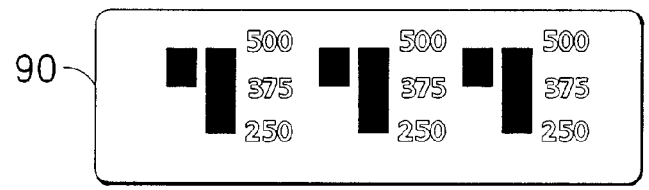
FIG. 17A is a schematic representation of a label having multiple minimum fill-volume indicators, maximum fill-volume indicators, and transitional fill-volume indicators in accordance with an embodiment of the present invention.
Figure 18:
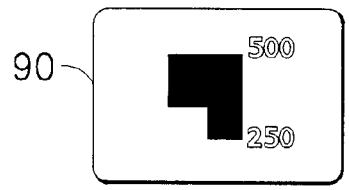
FIG. 18 is a schematic representation of a label having a minimum fill-volume indicator, a maximum fill-volume indicator, and a transitional fill-volume indicator capable of being disposed adjacent a sidewall of a collection container in accordance with an embodiment of the present invention.
Figure 18A:
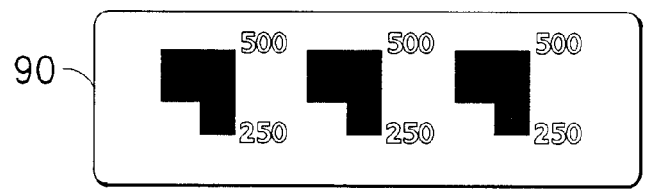
FIG. 18A is a schematic representation of a label having multiple minimum fill-volume indicators, maximum fill-volume indicators, and transitional fill-volume indicators in accordance with an embodiment of the present invention.
Figure 19:
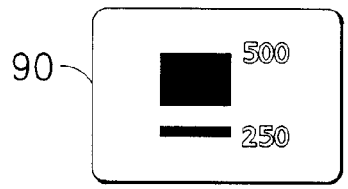
FIG. 19 is a schematic representation of a label having a minimum fill-volume indicator, a maximum fill-volume indicator, and a transitional fill-volume indicator capable of being disposed adjacent a sidewall of a collection container in accordance with an embodiment of the present invention.
Figure 19A:
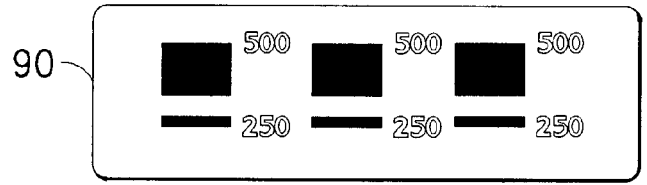
FIG. 19A is a schematic representation of a label having multiple minimum fill-volume indicators, maximum fill-volume indicators, and transitional fill-volume indicators in accordance with an embodiment of the present invention.
Figure 20:
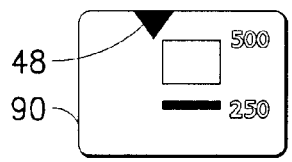
FIG. 20 is a schematic representation of a label having a minimum fill-volume indicator, a maximum fill-volume indicator, a transitional fill-volume indicator, and an alignment feature capable of being disposed adjacent a sidewall of a specimen collection container in accordance with an embodiment of the present invention.
Figure 21:
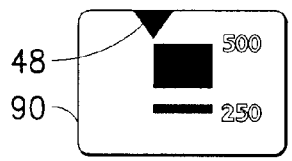
FIG. 21 is a schematic representation of a label having a minimum fill-volume indicator, a maximum fill-volume indicator, a transitional fill-volume indicator, and an alignment feature capable of being disposed adjacent a sidewall of a specimen collection container in accordance with an embodiment of the present invention.
Figure 22:
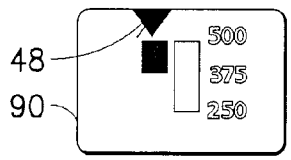
FIG. 22 is a schematic representation of a label having a minimum fill-volume indicator, a maximum fill-volume indicator, a transitional fill-volume indicator, and an alignment feature capable of being disposed adjacent a sidewall of a specimen collection container in accordance with an embodiment of the present invention.
Figure 23:
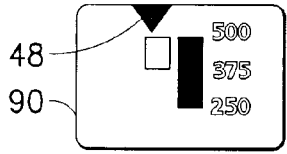
FIG. 23 is a schematic representation of a label having a minimum fill-volume indicator, a maximum fill-volume indicator, a transitional fill-volume indicator, and an alignment feature capable of being disposed adjacent a sidewall of a specimen collection container in accordance with an embodiment of the present invention.
Figure 24:
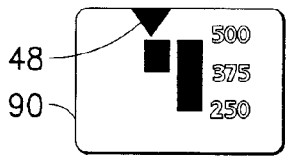
FIG. 24 is a schematic representation of a label having a minimum fill-volume indicator, a maximum fill-volume indicator, a transitional fill-volume indicator, and an alignment feature capable of being disposed adjacent a sidewall of a specimen collection container in accordance with an embodiment of the present invention.
Figure 25:
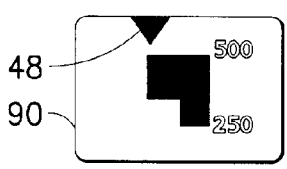
FIG. 25 is a schematic representation of a label having a minimum fill-volume indicator, a maximum fill-volume indicator, a transitional fill-volume indicator, and an alignment feature capable of being disposed adjacent a sidewall of a specimen collection container in accordance with an embodiment of the present invention.
Figure 26:
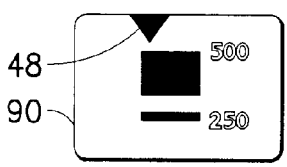
FIG. 26 is a schematic representation of a label having a minimum fill-volume indicator, a maximum fill-volume indicator, a transitional fill-volume indicator, and an alignment feature capable of being disposed adjacent a sidewall of a specimen collection container in accordance with an embodiment of the present invention.
Figure 27:
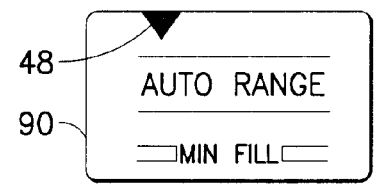
FIG. 27 is a schematic representation of a label having a minimum fill-volume indicator, a transitional fill-volume indicator, and an alignment feature capable of being disposed adjacent a sidewall of a specimen collection container in accordance with an embodiment of the present invention.
Figure 28:
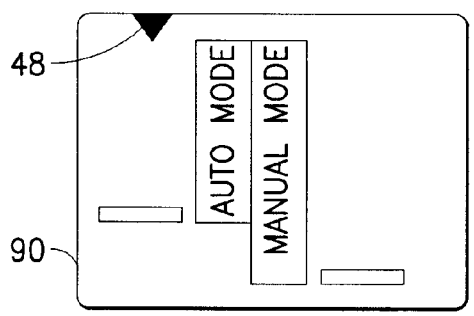
FIG. 28 is a schematic representation of a label having an alignment feature and a transitional fill-volume indicator indicating a first extraction process and a second extraction process capable of being disposed adjacent a sidewall of a specimen collection container in accordance with an embodiment of the present invention.

In yet a further configuration, as shown in FIGS. 12B-12D, in certain embodiments the first fill-volume indicator 60, the second fill-volume indicator 62, and the transitional fill-volume indicator 30 may each be offset from one another such that the none of the first fill-volume indicator 60, the second fill-volume indicator 62, and the transitional fill-volume indicator 30 are aligned. As shown in FIGS. 12B-12D, the transitional fill volume indicator may have a thickness 30a indicating a transition range which is offset from both the first fill-volume indicator 60 and the second fill-volume indicator 62. In a further embodiment, the transitional fill-volume indicator 30 may include a first transition 30b and a second transition 30c with the first volumetric interior indicated between the first fill-volume indicator 60 and the first transition 30b, and the second volumetric interior indicated between the second fill-volume indicator 62 and the second transition 30c.

As shown in FIGS. 13-19A, the transitional fill-line indicator 30 and any of the above-described configurations of the first fill-volume indicator 60 and the second fill-volume indicator 62 may be provided on a label 90 which may be provided on an outer surface 36 of a specimen collection container 10, as shown in FIG. 1.

In other configurations, one or more of the first and second fill-volume indicators 60, 62 may be defined by a polygonal figure, such as a block or bar, extending about a sidewall of the container. Each polygonal figure can act to define the scope of the corresponding fill-volume range by, for instance, having respective sides defining the upper and lower limits of the fill-volume range. The blocks may extend along a sidewall of the specimen collection container in the axial direction, with respect to the container. The axial extent of one block can differ from the axial extent of the other block to show the different volume ranges associated with the first and second fill-volume ranges. By way of example, the blocks may be disposed adjacent one another so that they share a common side, as seen in FIGS. 11 and 11A, or the blocks may be spaced from one another, as seen in FIGS. 10 and 10A, though these particular arrangements should not be seen as limiting. In another non-limiting embodiment, the specimen collection container 10 may comprise a single polygonal shape to define one fill-volume range, such as shown in FIGS. 6-7A. The shapes defining the fill-volume ranges can, independently, be shaded, colored, transparent, or translucent.

As shown in FIGS. 20-28, the transitional fill-volume indicator 30 and any of the above-described configurations of the first fill-volume indicator 60 and the second fill-volume indicator 62 may be provided on a label 90 which also includes first alignment symbology 48 which may be provided on an outer surface 36 of a specimen collection container 10 having second alignment symbology 50, as shown in FIG. 1.

During use, a medical practitioner may provide a volume of sample into the interior of the specimen collection container 10 such that the specimen is disposed below the transitional fill-volume indicator 30 if it is desired to remove the specimen therefrom by a first extraction process, such as by manual extraction. The medical practitioner may instead provide a volume of sample into the interior of the specimen collection container 10 such that at least a portion of the volume of specimen is disposed at or above the transitional fill-volume indicator 30 if it is desired to remove the specimen therefrom by the first extraction process or a second extraction process, such as by manual extraction or by automated extraction processes. Subsequent extraction of the sample from the specimen collection container 10 is therefore conducted by a first extraction process if the specimen is disposed below the transitional fill-volume indicator 30 when the sample collection container 10 is in the sampling orientation. Subsequent extraction of the sample from the specimen collection container 10 may therefore also be conducted by a second extraction process if the specimen is disposed at or above the transitional fill-volume indicator 30 when the sample collection container 10 is in the sampling orientation.

The invention claimed is:

1. A specimen collection container, comprising:
a top end, a closed bottom end, and a sidewall extending therebetween defining an interior;
a first fill-volume indicator adjacent the sidewall corresponding to a first interior fill-volume;
a second fill-volume indicator adjacent the sidewall corresponding to a second interior fill-volume, wherein the first interior fill-volume is less than the second interior fill-volume; and
a transitional fill-volume indicator adjacent the sidewall and positioned between the first fill-volume indicator and the second fill-volume indicator, with the first fill-volume indicator, the second fill-volume indicator, and the transitional fill-volume indicator aligned about a longitudinal axis of the container,
wherein a sample may be extracted from within the interior of the container by a first extraction process if the volume of sample is below the transitional fill-volume indicator in a sampling orientation, and in which a sample may be extracted from within the interior of the container by the first extraction process or a second extraction process if the volume of sample is above the transitional fill-volume indicator in the sampling orientation, the second extraction process being different than the first extraction process.

2. The specimen collection container of claim 1, wherein the first extraction process is a manual extraction process, and the second extraction process is an automated extraction process.

3. The specimen collection container of claim 1, wherein at least one of the first fill-volume indicator, the second fill-volume indicator, and the transitional fill-volume indicator are integrally formed with the sidewall of the container.

4. The specimen collection container of claim 1, wherein at least one of the first fill-volume indicator, the second fill-volume indicator, and the transitional fill-volume indicator are at least partially raised with respect to a surface of the sidewall of the container.

5. The specimen collection container of claim 1, wherein at least one of the first fill-volume indicator, the second fill-volume indicator, and the transitional fill-volume indicator are at least partially recessed with respect to a surface of the sidewall of the container.

6. The specimen collection container of claim 1, wherein at least one of the first fill-volume indicator, the second fill-volume indicator, and the transitional fill-volume indicator are printed on a surface of the sidewall of the container.

7. The specimen collection container of claim 1, wherein at least one of the first fill-volume indicator, the second fill-volume indicator, and the transitional fill-volume indicator are at least partially textured with respect to a surface of the sidewall of the container.

8. The specimen collection container of claim 1, wherein at least one of the first fill-volume indicator, the second fill-volume indicator, and the transitional fill-volume indicator comprises a color contrast or visual effects contrast with respect to at least one of a portion of the sidewall of the container and the other of the first fill-volume indicator, the second fill-volume indicator, and the transitional fill-volume indicator.

9. The specimen collection container of claim 1, further comprising a label including at least one of the first fill-volume indicator, the second fill-volume indicator, and the transitional fill-volume indicator disposed at least partially on the sidewall of the container.

10. The specimen collection container of claim 9, wherein at least one of the label and the sidewall of the container includes a first alignment symbology and the other of the label and the sidewall of the container includes a second alignment symbology, wherein the first alignment symbology and the second alignment symbology provide corresponding alignment.

11. The specimen collection container of claim 1, wherein at least one of the first fill-volume indicator, the second fill-volume indicator, and the transitional fill-volume indicator further comprises identifying information.

12. The specimen collection container of claim 11, wherein the identifying information identifies at least one of the first extraction process and the second extraction process.

13. The specimen collection container of claim 11, wherein the identifying information identifies corresponding fill-volumes.

14. The specimen collection container of claim 1, wherein at least one of the first fill-volume indicator, the second fill-volume indicator, and the transitional fill-volume indicator is a line disposed substantially perpendicular to the longitudinal axis of the container.

15. The specimen collection container of claim 1, wherein at least one of the first fill-volume indicator, the second fill-volume indicator, and the transitional fill-volume indicator comprise a window through which a specimen may be viewed.

16. The specimen collection container of claim 1, wherein at least one of a range extending between the first fill-volume indicator and the transitional fill-volume indicator, and a range extending between the transitional fill-volume indicator and the second fill-volume indicator comprises an indicator region.

17. The specimen collection container of claim 16, wherein the indicator region comprises a color contrast or a visual effects contrast with at least a portion of the sidewall of the container.

18. The specimen collection container of claim 16, wherein the indicator region comprises a first region corresponding to the range extending between the first fill-volume indicator and the transitional fill-volume indicator, and a second region corresponding to the range extending between the transitional fill-volume indicator and the second fill-volume indicator.

19. The specimen collection container of claim 1, wherein the first fill-volume indicator is a minimum fill-volume indicator that defines a minimum functional volume between the closed bottom end and the minimum fill-volume indicator, and wherein the second fill-volume indicator is a maximum fill-volume indicator that defines a maximum functional volume between the closed bottom end and the maximum fill-volume indicator.

* * * * *